United States Patent [19] … [11] 4,376,778
Ezaki et al. … [45] Mar. 15, 1983

[54] ANTIBIOTIC SUBSTANCES AND PROCESSES FOR PRODUCTION THEREOF

[75] Inventors: Norio Ezaki; Takashi Shomura; Tomizo Niwa, all of Yokohama; Michio Kojima, Tokyo; Shigeharu Inouye, Yokohama; Tatsuo Ito, Isehara, all of Japan

[73] Assignee: Meiji Seika Kaisha, Ltd., Tokyo, Japan

[21] Appl. No.: 218,975

[22] Filed: Dec. 22, 1980

[30] Foreign Application Priority Data

Dec. 24, 1979 [JP] Japan .................. 54-166926

[51] Int. Cl.³ .................. C07D 207/42; A61K 31/40
[52] U.S. Cl. .................. 424/274; 548/557
[58] Field of Search .................. 260/326.9; 424/274

[56] References Cited

U.S. PATENT DOCUMENTS 3,932,458  1/1976  Baily .................. 260/326.9

FOREIGN PATENT DOCUMENTS 2472611  7/1981  France .

OTHER PUBLICATIONS

Koyama et al.; Chem. Abs., vol. 96:103936w (1982).
Ezaki et al.; Chem. Abs., vol. 96:4942p (1982).

Primary Examiner—Mary C. Lee
Attorney, Agent, or Firm—Sughrue, Mion, Zinn, Macpeak & Seas

[57] ABSTRACT

Antibiotics, designated as SF-2080A substance and SF-2080B substance, are described, and are obtained by cultivating an SF-2080 substance-producing strain belonging to the genus Streptomyces, for example, Streptomyces sp. SF-2080 (FERM-P No. 5072, ATCC No. 31673), in a nutrient medium, and recovering the desired substance from the culture.

2 Claims, 4 Drawing Figures

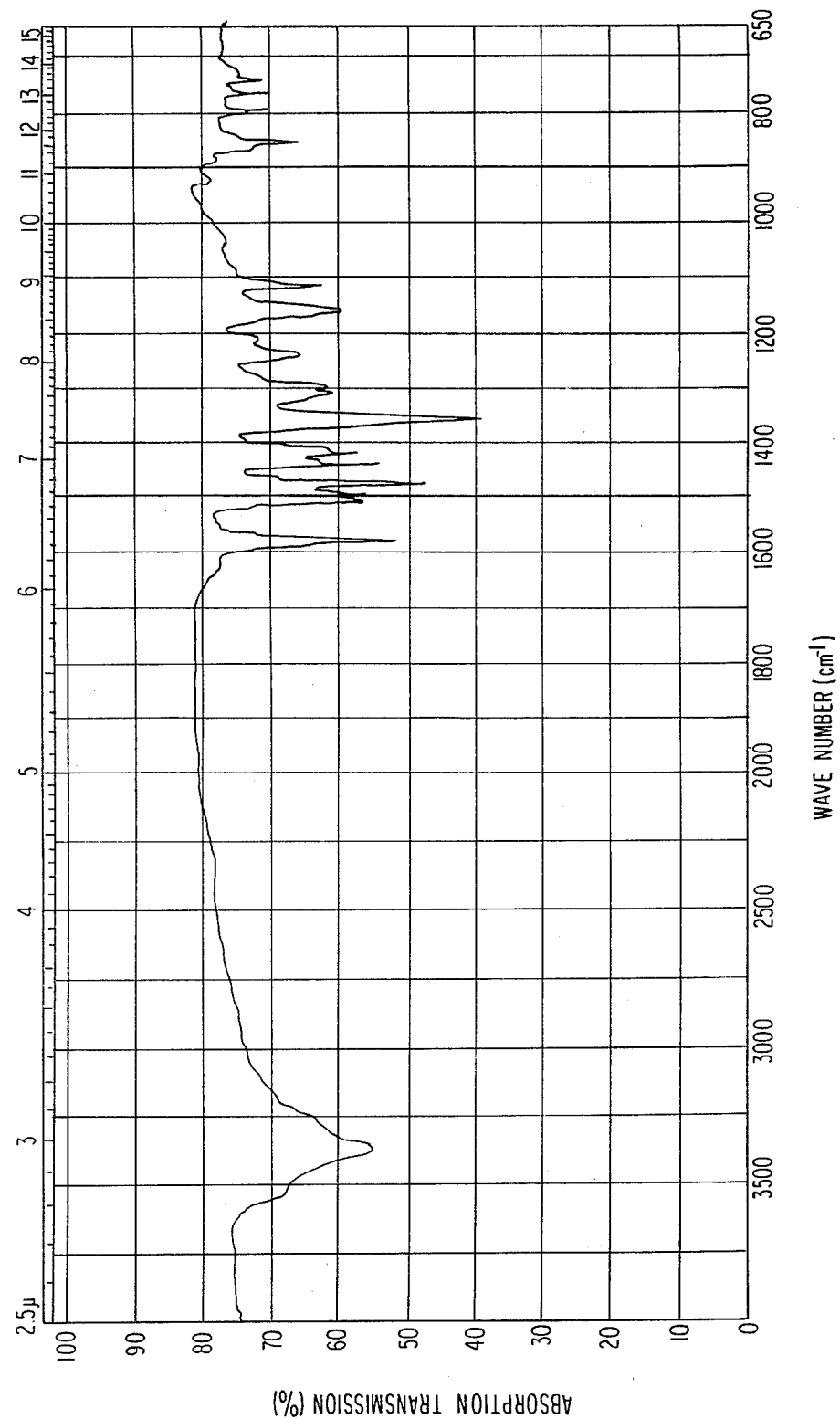

ANTIBIOTIC SUBSTANCES AND PROCESSES FOR PRODUCTION THEREOF

BACKGROUND OF THE INVENTION

This invention relates to a novel antibiotic and a process for production of the same. More particularly it relates to a novel antibiotic SF-2080A substance and/or SF-2080B substance which are obtained by cultivating an SF-2080 substance-producing strain belonging to the genus Streptomyces in a nutrient medium and recovering the SF-2080 substances so produced from the culture, and a process for producing the antibiotic SF-2080A substance and/or SF-2080B substance.

It has been known that various microbial species, e.g., of the genus Streptomyces, may produce antibiotics, upon cultivation in nutrient media containing assimilable carbon and nitrogen sources. However, a continuing need exists for new and useful antibiotic substances.

SUMMARY OF THE INVENTION

This invention provides novel antibiotics designated, respectively, as SF-2080A substance and SF-2080B substance, and a process for producing SF-2080A substance and SF-2080B substance by cultivating an SF-2080 substance-producing strain belonging to the genus Streptomyces in a nutrient medium.

BRIEF DESCRIPTION OF THE DRAWINGS

FIG. 4 is an infrared absorption spectrum of the SF-2080B substance as measured in a potassium bromide tablet.

DETAILED DESCRIPTION OF THE INVENTION

Figure 1:
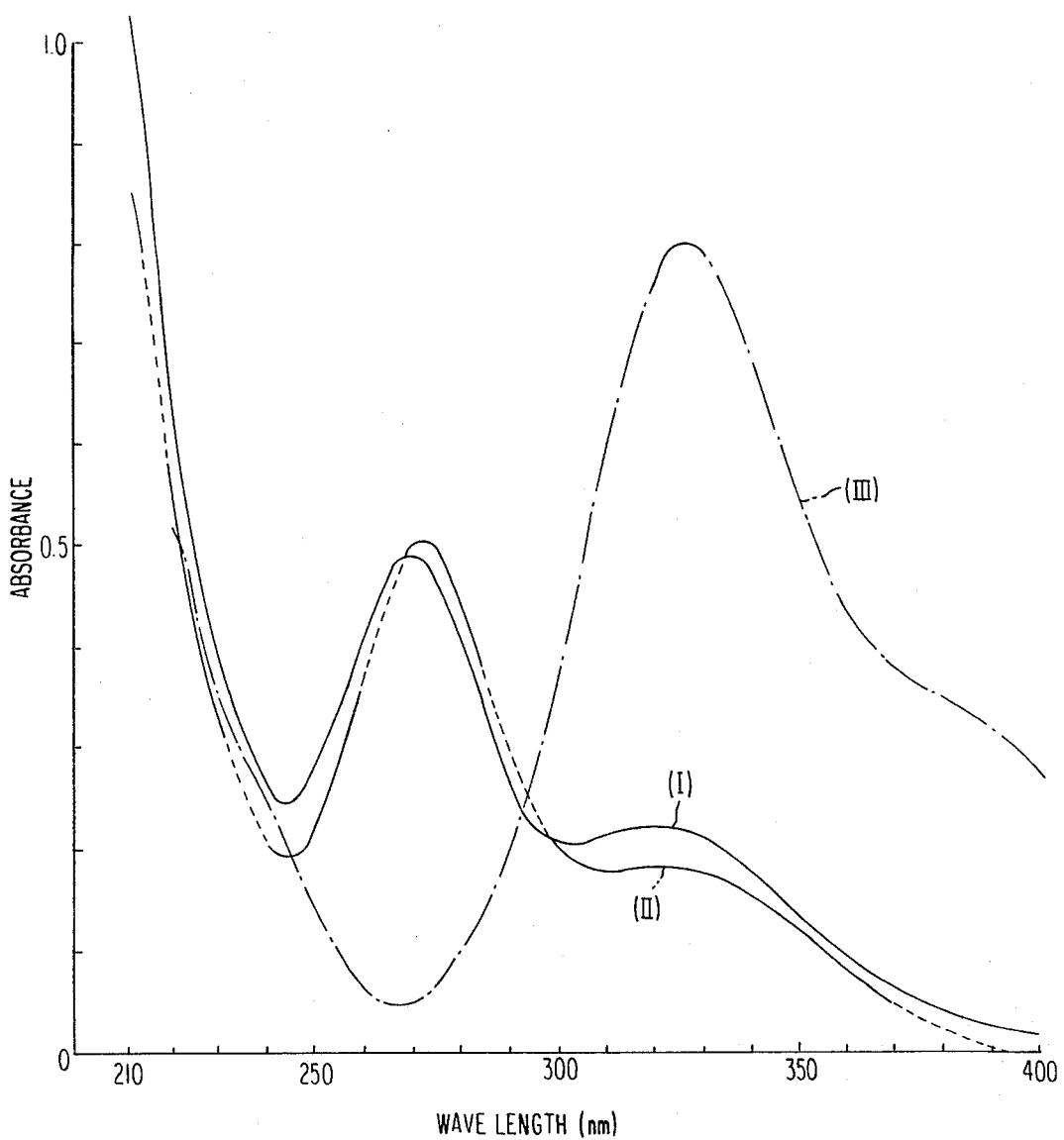
FIG. 1 is an ultraviolet absorption spectrum of the SF-2080A substance as measured at a concentration of 10 mcg/ml (micrograms/milliliter) in (I) methanol, (II) acidic methanol (i.e., in 0.01-N HCl methanol solution) and (III) alkaline methanol (i.e., in 0.01-N NaOH methanol solution)

As the antibiotic SF-2080 substance-producing strain as used in this invention (the term "antibiotic SF-2080 substance" as used herein includes both SF-2080A substance and SF-2080B substance), any strain capable of producing the antibiotic SF-2080 substance in an amount sufficient to be recovered from the fermentation broth can be used. An example of such strains is Streptomyces sp. SF-2080 isolated from a soil sample collected from the riverbed of River Chikuma in Nagano-City, Nagano-Prefecture, Japan.

The characteristics of the Streptomyces sp. SF-2080 are as follows:

(I) Morphological Characteristics

The substrate mycelium is abundantly branched and stretches in a wave-form. The diameter of the hypha is 0.5 to 0.6 micron. Usually, no fragmentation of the substrate mycelium is observed in either agar culture medium or liquid medium. Aerial mycelium is not formed at all on the usually used agar culture medium. Spore, sporangium, zoospore, sclerotium, synnemata, etc., have not yet been observed.

(II) Culture Characteristics

The culture characteristics of the Streptomyces sp. SF-2080 were observed according to the method as described in E. G. Shirling & D. Gottlieb, *International Journal of Systematic Bacteriology*, Vol. 16, pp. 313–340 (1966). The observation was carried out after cultivation at 28° C. for 14 days. The culture characteristics with respect to various media are shown in Table 1.

TABLE 1

| Culture Medium | Growth and Reverse Color | Aerial Mycelium | Soluble Pigment |
|---|---|---|---|
| Sucrose-Nitrate Agar | Very scant growth, colorless | None | Not produced |
| Glucose-Asparagine Agar | Very scant growth, colorless | None | Not produced |
| Glycerol-Asparagine Agar | Scant growth, colorless | None | Not produced |
| Calcium Malate Agar | Very scant growth, colorless | None | Not produced |
| Starch Agar | Very scant growth, colorless | None | Not produced |
| Yeast Malt Agar | Moderate growth, in a thin skin form, colorless to light yellowish brown | None | Not produced |
| Tyrosine Agar | Scant to moderate growth, colorless to light yellowish brown | None | Not produced |
| Nutrient Agar | Moderate growth, light yellowish brown | None | Not produced |
| Oatmeal Agar | Scant to moderate growth, colorless | None | Not produced |
| Bennett's Agar | Moderate growth, colorless to light yellowish brown | None | Not produced |

(III) Physiological Characteristics (1) Growth Temperature Range: Grows in yeast malt agar at a range of from 15° C. to 45° C., and grows well at from 25° C. to 34° C.

(2) Liquefaction of Gelatin: Positive (cultivation at 20° C. for 21 days)

(3) Hydrolysis of Starch: Positive (weak, cultivation at 28° C. for 14 days)

(4) Action on Skim Milk: Neither peptonization nor coagulation occurs on cultivation at 28° C. for 14 days.

(5) Reduction of Nitrate: Positive (cultivation at 28° C. for 14 days)

(6) Salt Resistance: Growth occurs at 1.5%, but not at 3.0%.

(7) Production of Melanine-Like Pigments: Negative

(IV) Utilization of Carbon Sources

A basic culture medium consisting of 0.5% of yeast extract (Difco), 0.1% of calcium carbonate and 1.5% of agar (Difco) was employed to examine the utilization of carbon sources. The results are shown in Table 2.

TABLE 2

| Carbon Source | Growth* |
|---|---|
| D-Glucose | + |
| D-Xylose | + |
| D-Fructose | − |
| L-Arabinose | − |
| D-Mannitol | − |
| i-Inositol | − |
| L-Rhamnose | + |
| Sucrose | − |
| Raffinose | − |

*Symbol "+" means utilizable.
Symbol "−" means not utilizable.

(V) Composition of Cell Wall

Analysis according to Becker, et al., Appl. Microbiol., Vol. 13, p. 236 (1965) confirmed that diaminopimelic acid contained in the cell wall composition is of LL type.

Judging from the above characteristics, Streptomyces sp. SF-2080 belongs to the order *Actinomycetales* and is a mesophilic and an actinomycetes in which no fragmentation of the substrate mycelium is observed, and which contains LL-diaminopimelic acid in the cell wall.

It is, however, not possible at the present time to conclusively determine the genus to which the SF-2080 strain belongs because such morphological characteristics as spore, sporangium, zoospore, sclerotium, and synnemata which are necessary for determination of the genus of actinomycetes have not yet been made clear. However, taking into account the fact that the SF-2080 strain contains LL-diaminopimelic acid in the cell wall, it appears most likely that the SF-2080 strain is an undetermined species belonging to the genus of Streptomyces, and therefore have tentatively named it Streptomyces sp. SF-2080.

This strain has been deposited as Streptomyces sp. SF-2080 in the Fermentation Research Institute, Agency of Industrial Science and Technology, Ministry of International Trade and Industry of Japan under the accession number of FERM-P No. 5072 (on July 4, 1979) and in the American Type Culture Collection (ATCC) under ATCC number 31673 (on July 28, 1980).

The SF-2080 strain easily varies in its properties, as is the case with other actinomycetes strains. Such variation can be caused artificially by irradiating with, for example, ultraviolet rays, X-rays, high frequency waves or radioactive rays, and chemicals. Therefore, all variants as well as mutants can be used in the process of this invention so long as they have the ability to produce the SF-2080A substance and/or SF-2080B substance.

In accordance with the process of this invention, the above-described strain is cultivated in a medium containing nutrients which are assimilable by known microorganisms. Such nutrients can be known materials conventionally used in cultivation of actinomycetes strains.

Examples of carbon sources which can be used include glucose, glycerin, sucrose, starch, dextrin, maltose syrup, molasses, soybean oil, etc. Examples of nitrogen sources which can be used include soybean meal, wheat germ, cottonseed meal, meat extract, peptone, yeast extract, dry yeast, corn steep liquor, ammonium sulfate, sodium nitrate, etc. Additionally, if desired, inorganic salts such as calcium carbonate, sodium chloride, cobalt chloride, phosphates, etc., as well as those organic and inorganic materials which enhance microbial production of the antibiotic SF-2080 substance can appropriately be added.

The submerged cultivation method under aerated conditions is most suitable for cultivation of the antibiotic SF-2080 substance-producing strain as is often the case with the production of known antibiotics. The suitable temperature range for the cultivation is from 25° C. to 34° C., and, preferably, it is carried out at 28° C. to 32° C. The production of SF-2080 substances reaches a maximum in from 2 to 7 days in both shake-culture and tank-culture, and the SF-2080 substances are accumulated in the cultivation broth.

The determination of the antibiotic SF-2080 substances can be carried out by a combination of the bioassay using *Sarcina lutea* as a test organism and thin layer chromatography using silica gel.

The SF-2080A substance and SF-2080B substance have their respective physical and chemical properties as hereinafter described. According to these properties, they can be extracted and purified. The following method can be efficiently used:

To a filtrate obtained by filtering off solid matter (i.e., mycelia) from a culture broth containing the desired substances is added an organic solvent which is not freely miscible with water, such as ethyl acetate, etc. They are then mixed to extract the desired substances. On the other hand, an organic solvent which is freely miscible with water, such as acetone, methanol, etc., is added to the solid matter (i.e., mycelia) to extract the desired substances therefrom. After evaporating off the organic solvent, the desired substances are extracted with an organic solvent such as ethyl acetate, etc. Extracts from the filtrate and the solid matter (i.e., mycelia) are combined. The solvent is evaporated to obtain an oily substance. A solvent such as n-hexane, etc., is added to the oily substance to extract impurities. The residue so obtained is dissolved in methanol or the like, and the resulting solution is subjected to column chromatographies using carriers such as silica gel, alumina, gel filtering media for molecular sieve, etc., to isolate the antibiotic SF-2080A substance and/or SF-2080B substance. The SF-2080A substance and/or SF-2080B substance so isolated is dissolved in a small amount of methanol and then crystallized to obtain the corresponding crystals. The crystals of the SF-2080A substance and/or SF-2080B substance, when analyzed by thin layer chromatography using various solvent systems, provide a single spot. This tends to indicate that they are each a pure product.

The physical and chemical properties of each of the SF-2080A substance and the SF-2080B substance as obtained by the above-described method are as follows:

TABLE 3

| | | SF-2080A Substance | SF-2080B Substance |
|---|---|---|---|
| 1. | Elemental | C, 27.06%; H, 1.17%; N, 14.84%; | C, 36.79%; H, 1.67%; N, 7.95%; |

TABLE 3-continued

| | | SF-2080A Substance | SF-2080B Substance |
|---|---|---|---|
| | Analysis (% by weight) | Cl, 39.23% | Cl, 39.89% |
| 2. | Molecular Weight | 181 (mass spectrum) | 356 (mass spectrum) |
| 3. | Molecular Formula | $C_4H_2N_2O_2Cl_2$ | $C_{11}H_6N_2O_3Cl_4$ |
| 4. | Melting Point | 205° to 207° C. (decomposition) | 202° to 211° C. (decomposition) |
| 5. | Optical Rotation | $[\alpha]_D^{25} = 0$ (C = 0.5, methanol) | $[\alpha]_D^{25} = 0$ (C = 0.5, methanol) |
| 6. | Ultraviolet Absorption Spectrum | Shown in FIG. 1. The absorption maximums are 269 nm ($E_{1cm}^{1\%}$ 490) and 320 nm ($E_{1cm}^{1\%}$ 230) in a methanol solution; 271 nm ($E_{1cm}^{1\%}$ 500) and 320 nm($E_{1cm}^{1\%}$ 190) in a 0.01-N hydrochloric acid methanol solution; and 220 nm ($E_{1cm}^{1\%}$ 520) and 325 nm ($E_{1cm}^{1\%}$ 800) in a 0.01-N sodium hydroxide methanol solution. | Shown in FIG. 3. The absorption maximums are 276 nm ($E_{1cm}^{1\%}$ 300) and 328 nm ($E_{1cm}^{1\%}$ 170) in a methanol solution; 277 nm ($E_{1cm}^{1\%}$ 310) and 335 nm ($E_{1cm}^{1\%}$ 150) in a 0.01-N hydrochloric acid methanol solution; and 245 nm ($E_{1cm}^{1\%}$ 570) and 313 nm ($E_{1cm}^{1\%}$ 570) in a 0.01-N sodium hydroxide methanol solution. |
| 7. | Infrared Absorption Spectrum | Shown in FIG. 2. The absorption bands, as determined using the potassium bromide tablet method, are 3270, 3150, 1570, 1510, 1480, 1400, 1360, 1280 1200, 1140, 1070, 960, 830, 820, 750 cm$^{-1}$. | Shown in FIG. 4. The absorption bands, as determined using the potassium bromide tablet method, are 3360, 1580 1510, 1490, 1480, 1440, 1420, 1360, 1310, 1290, 1240, 1210, 1160, 1110, 930, 890, 860, 800, 770, 740 cm$^{-1}$. |
| 8. | Color Reactions | positive: iodine reaction and Lemieux reaction<br>negative: ninhydrin reaction and ferric chloride reaction | positive: iodine reaction and Lemieux reaction<br>negative: ninhydrin reaction and ferric chloride reaction |
| 9. | Appearance and Color of the Substance | light brown to yellow needle-shaped crystals | yellow needle-shaped crystals |
| 10. | Electrical Properties | behaves as electrically neutral substance on High Voltage Paper Electrophoresis | behaves as electrically neutral substance on High Voltage Paper Electrophoresis |
| 11. | Rf Values on Thin layer Chromatography (silica gel, 60F$_{254}$ produced by E. Merck Co.) | 0.68 (benzene/acetone, 2:1 by volume)<br>0.73 (chloroform/methanol, 10:1 by volume) | 0.73 (benzene/acetone, 2:1 by volume)<br>0.80 (chloroform/methanol, 10:1 by volume) |
| 12. | Solubility | easily soluble in methanol, acetone; soluble in chloroform; sparingly soluble in water, n-hexane | easily soluble in methanol, acetone; soluble in chloroform; sparingly soluble in water, n-hexane |
| 13. | Apparent Structural Formula | 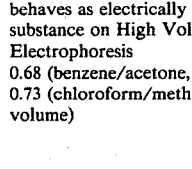 | 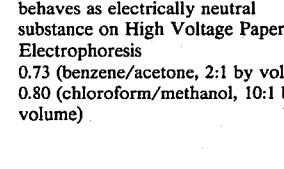 |

The minimum inhibitory concentrations of the SF-2080A substance and SF-2080B substance against various microorganisms as measured by the agar dilution method are shown in Table 4 below. The SF-2080A substance is generally effective against all strains of bacteria tested, whereas the SF-2080B substance is very effective against a limited number of strains, but it is less active or lacks toward the others.

The acute toxicity of each of the SF-2080A substance and the SF-2080B substance was measured by intraperitoneal administration in mice. By administration of the SF-2080A substance at a dose of 30 mg/kg, all mice died, but at a dose of 10 mg/kg, all mice survived. On the other hand, by administration of the SF-2080B substance at a dose of 100 mg/kg, ⅔ of the mice survived. The SF-2080A substance and SF-2080B substance are therefore useful as medicines, pesticides, animal medicines, sterilizing agents, etc., or materials to be converted thereinto.

TABLE 4

| | Minimum Inhibitory Concentration (mcg/ml) | |
|---|---|---|
| Test Organism | SF-2080A Substance | SF-2080B Substance |
| *Staphylococcus aureus* FDA 209P JC-1 | 1.56 | 0.20 |
| *Staphylococcus aureus* Smith | 3.13 | 0.20 |
| *Staphylococcus epidermidis* ATCC 14990 | 3.13 | 0.10 |
| *Bacillus subtilis* ATCC 6633 | 1.56 | 0.10 |
| *Escherichia coli* NIHJ JC-2 | 6.25 | 100 |
| *Escherichia coli* K-12 IAM 1264 | 6.25 | 100 |
| *Salmonella typhi* O-901-W | 6.25 | 50 |
| *Shigella dysenteriae* Shigae | 3.13 | 50 |
| *Klebsiella pneumoniae* ATCC 27763 | 6.25 | >100 |
| *Proteus vulgaris* OX-19 | 6.25 | 0.78 |
| *Serratia marcescens* No. 1 | 6.25 | >100 |
| *Pseudomonas aeruginosa* IAM 1007 | 6.25 | >100 |
| *Cryptococcus neoformans* Cr-1 | 25 | >100 |
| *Trichophyton asteroides* | 3.12 | >100 |
| *Trichophyton interdigital* | 1.56 | 100 |
| *Aspergillus fumigatus* | 25 | >100 |
| *Pyricularia oryzae* | 0.8 | 3.13 |
| *Diaporthe citri* | 0.8 | 0.4 |

Further, the SF-2080A substance not only has antibacterial activity, but also inhibits the growth of fungi.

The minimum growth inhibitory concentration (MIC) against each test strain according to the plate dilution method is shown below:

TABLE 5

| Test Strain | MIC (mcg/ml) |
|---|---|
| Candida albicans C-A-24 | 100 |
| Cryptococcus neoformans CR-1 | 25 |
| Trichophyton asteroides | 3.12 |
| Trichophyton interdigitale | 1.56 |
| Aspergillus fumigatus | 25 |

This indicates that the SF-2080A substance is also a useful compound as an antimycotic agent.

The SF-2080A substance can be applied onto the affected area, for example, by coating it as an ointment or a solution. A formulation example as a liquid preparation with a skin-permeating agent added thereto is shown in Table 6.

TABLE 6

| SF-2080A Substance | 0.25 g |
|---|---|
| Diethyl Sebacate | 2.5 ml |
| Pharmacopoeial Distilled Water | 2.5 ml |
| Ethanol to make | 25 ml |

An infection treatment test of guinea pigs infected by a strain of Trichophyton asteroides on their backs was carried out using the liquid preparation having formulation as shown in Table 6. This test confirmed that as compared with pyrrolnitrin and clotrimazole, as used as control medicines, SF-2080A substance of this invention exhibited excellent therapeutic effects in both the observation with the naked eye and tests for cultivation positive ratio (cultivation tests of cured parts initially infected, and there observed marked decline of infected organism).

By comparing the physical and chemical properties and biological characteristics of the SF-2080A substance and SF-2080B substance with those of the known antibiotics, it was found that they are each novel antibiotics.

The following examples are given to illustrate this invention in greater detail. It is to be noted that many modifications and variations can be made without departing from the scope of the invention.

EXAMPLE 1

A liquid medium of a composition comprising 1 wt% soluble starch, 1 wt% glucose, 0.5 wt% peptone, 0.3 wt% yeast extract, 0.2 wt% soybean meal, 0.2 wt% meat extract, and 0.1 wt% calcium carbonate was prepared. Then, 20 ml portions of the liquid medium so prepared were separately introduced into a 100 ml Erlenmeyer flask and sterilized. Streptomyces sp. SF-2080 (FERM-P No. 5072, ATCC No. 31673) was inoculated in the liquid medium and incubated on a shaker at 28° C. for 5 days to prepare First Seed Culture. The same procedure as above was repeated wherein the volume was gradually increased, to prepare a Second Seed Culture (i.e., the First Seed Culture was inoculated in 80 ml of the liquid medium introduced in 500 ml Erlenmeyer flask and incubated at 28° C. for 2 days to prepare the Second Seed Culture) and a Third Seed Culture (i.e., the Second Seed Culture was inoculated in 800 ml of the liquid medium introduced in 5 l Erlenmeyer flask and incubated at 28° C. for 2 days to prepare the Third Seed Culture).

Thereafter, 35 l of a culture medium having the composition comprising 2 wt% maltose syrup, 0.15 wt% soybean oil, 1 wt% soybean meal, 0.25 wt% distiller's solubles, 0.5 wt% Fermamedia (trademark, produced by Traders Oil Mill Co., Texas), 0.0005 wt% ferrous sulfate, 0.00005 wt% nickel chloride, 0.00005 wt% cobalt chloride and 0.1 wt% calcium carbonate was charged into a 50 l stainless steel fermentation tank, sterilized and then inoculated with 800 ml of the Third Seed Culture. The cultivation was carried out at 28° C. while aerating and stirring. The amount of aeration and the number of rotation were 35 l/minute and 300 rpm, respectively.

After a period of 120 hours, the cultivation was stopped and the culture was separated into a solid fraction and a filtrate by filtration. 20 l of ethyl acetate was added to 25 l of the filtrate and stirred to extract the effective component. Then, the ethyl acetate layer was isolated. On the other hand, 10 l of a 50% aqueous solution of acetone was added to the solid fraction and stirred to extract the effective component. The solid fraction was then filtered off. Thereafter, the filtrate was concentrated under reduced pressure to evaporate acetone and then, 2.5 l of ethyl acetate was added and stirred to extract the effective component. Thereafter, the ethyl acetate layer was isolated and combined with the ethyl acetate extraction layer from the filtrate. Upon the concentration of the resulting mixture under reduced pressure, about 30 ml of a tarry substance was obtained.

Upon addition of n-hexane to the tarry substance as obtained above, the desired substances were virtually insoluble in the n-hexane and remained as precipitates. After removal of the supernatant liquid, the precipitates were applied onto a 700 ml column of Wako Gel C-100 (produced by Wako Pure Chemical Industries Ltd.) which had previously been packed with chloroform, and were eluted with chloroform to obtain active fractions. These active fractions were concentrated to obtain 800 mg of an oily product.

The oily product so obtained was dissolved in about 5 ml of methanol, subjected to a 600 ml column of Sephadex LH-20 (produced by Pharmacia Co., Sweden) and eluted with methanol to separate 30 ml fractions. The SF-2080A substance was eluted in Fractions 18 to 21, and the SF-2080B substance was eluted in Fractions 25 to 30. In Fractions 22 to 24, a mixture of the SF-2080A substance and the SF-2080B substance was eluted. Fractions 22 to 24 were combined, concentrated, and again separated by chromatography using Sephadex LH-20.

Thus, 230 mg of the SF-2080A substance and 200 mg of the SF-2080B substance were obtained. They were each dissolved in a small amount of methanol and precipitated as crystals to obtain 90 mg of the SF-2080A substance and 80 mg of the SF-2080B substance.

EXAMPLE 2

Hairs were pulled off from a white Hartly guinea pig (4 guinea pigs per group) at 4 areas of the back thereof (2 areas on each side, 4×6 cm) and a Trichophyton asteroides-floating solution (liquid Sabouraud's culture medium; number of living cells: $2 \times 10^7$/ml) was infected with a brush in an amount of 0.5 ml per each area. After 2 days from the infection, 0.25 ml of a 1% solution of SF-2080A substance (see Table 6) was applied at one area on each side, once a day and continuously for 8 days.

The same procedure as above was carried out, except using a 1% solution of pyrrolnitrin and a 1% solution of clotrimazole. Guinea pigs so treated were compared with those to which no treatment was applied.

In the determination of the effect by the observation with the naked eye, as shown in Table 7, SF-2080A substance produced the best treatment effect in all the thickening of the affected skin, flush, and scale.

TABLE 7

| Effect | SF-2080A Substance | Pyrrol-nitrin* | Clotrimazole** |
|---|---|---|---|
| Thickening | Markedly effective | Effective | Effective |
| Flush | Markedly effective | Ineffective | Ineffective |
| Scale | Markedly effective ~Effective | Ineffective | Effective |

*Pyrrolnitrin:

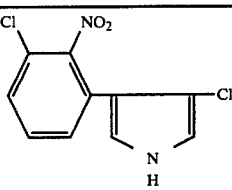

**Clotrimazole:

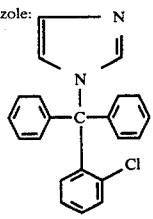

After treatment for 8 days, 3 skin pieces were collected from each affected area and cultivated on a Sabouraud's agar plate for 7 days to observe the infected organism cultivation positive ratio.

In the SF-2080A substance-dosed group, as compared with the pyrrolnitrin-dosed group, the clotrimazole-dosed group and the no treatment group, an evident decrease in the cultivation positive ratio was observed (see Table 8).

TABLE 8

| Day of Cultivation | SF-2080A Substance (%) | Pyrrol-nitrin (%) | Clotrimazole (%) | Non-Treatment (%) |
|---|---|---|---|---|
| 3 | 25 | 62 | 75 | 100 |
| 5 | 37 | 87 | 96 | 100 |
| 7 | 37 | 87 | 96 | 100 |

While the invention has been described in detail and with reference to specific embodiments thereof, it will be apparent to one skilled in the art that various changes and modifications can be made therein without departing from the spirit and scope thereof.

Figure 2:
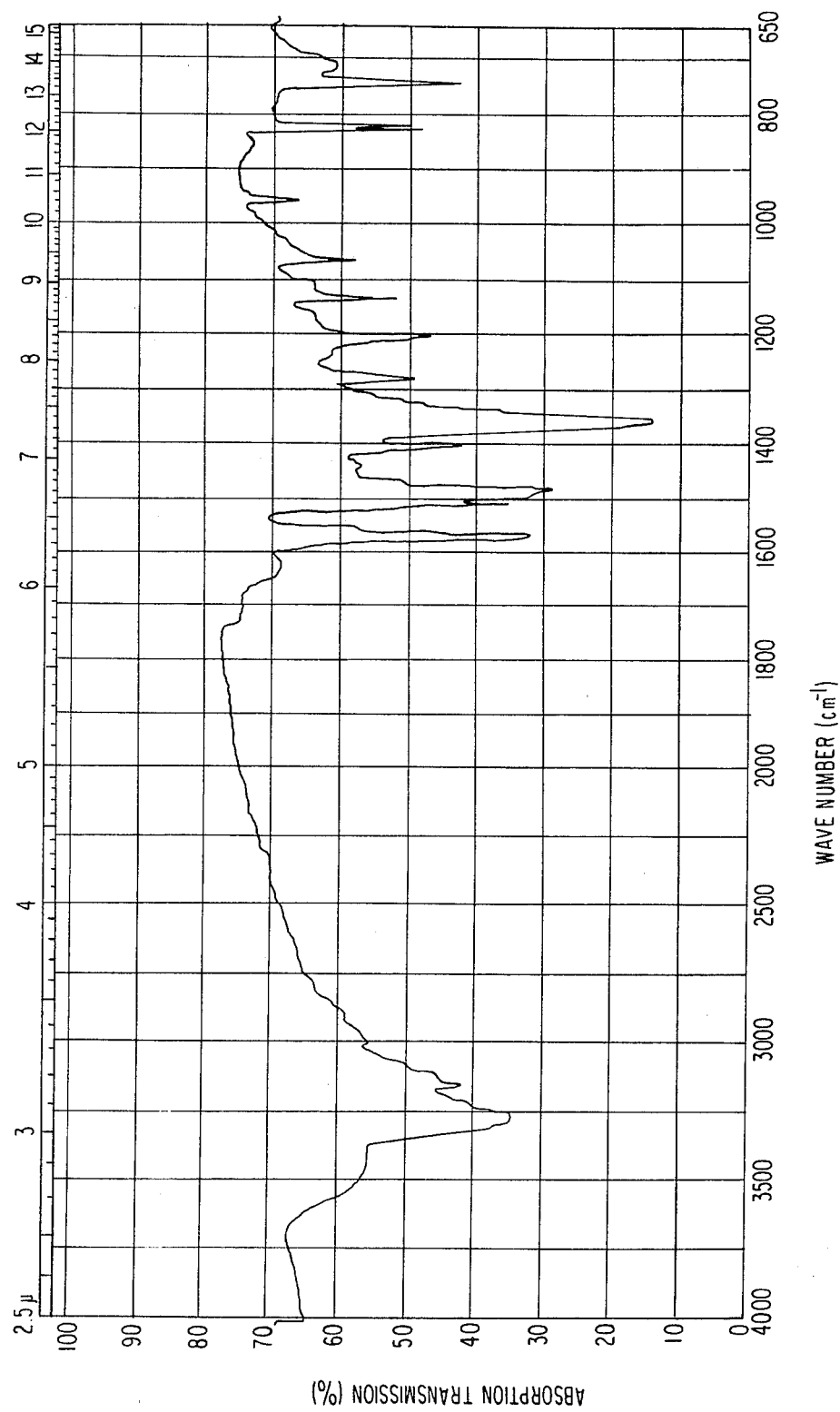
FIG. 2 is an infrared absorption spectrum of the SF-2080A substance as measured in a potassium bromide tablet.
Figure 3:
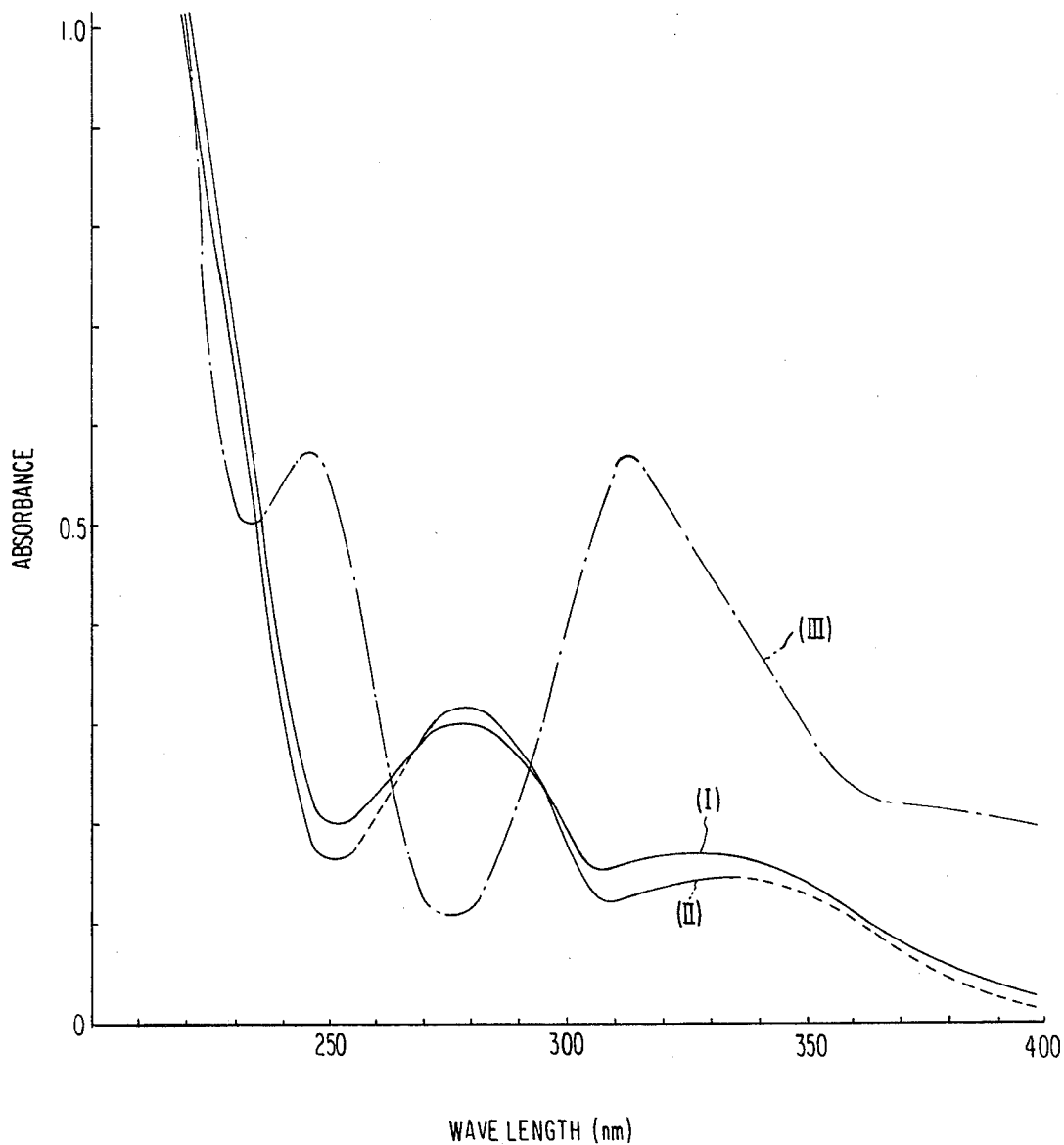
FIG. 3 is an ultraviolet absorption spectrum of the SF-2080B substance as measured at a concentration of 10 mcg/ml in (I) methanol, (II) acidic methanol (i.e., in 0.01-N HCl methanol solution) and (III) alkaline methanol (i.e., in 0.01-N NaOH methanol solution)

What is claimed is:
1. An SF-2080A substance having the following properties:
Elemental Analysis (by weight): C, 27.06%; H, 1.17%; N, 14.84%; Cl, 39.23%;
Molecular Weight: 181 (according to mass spectrum);
Molecular Formula: $C_4H_2N_2O_2Cl_2$;
Melting Point: 205° to 207° C. (with decomposition);
Optical Rotation: $[\alpha]_D^{25}=0$ (C=0.5, methanol);
Ultraviolet Absorption Spectrum: as shown in FIG. 1: The absorption maximums are 269 and 320 nm in a methanol solution, 271 and 320 nm in a 0.01-N hydrochloric acid methanol solution, and 220 and 325 nm in a 0.01-N sodium hydroxide methanol solution;
Infrared Absorption Spectrum: as shown in FIG. 2: The absorption bands, as determined using the potassium bromide tablet method, are 3270, 3150, 1570, 1510, 1480, 1400, 1360, 1280, 1200, 1140, 1070, 960, 830, 820, 750 $cm^{-1}$;
Color Reactions: positive for the iodine reaction and Lemieux reaction, and negative for the ninhydrin reaction and ferric chloride reaction;
Appearance and Color: light brown to yellow needle-shaped crystals;
Electrical Properties: behaves as neutral substance on High Voltage Paper Electrophoresis;
Rf Values on Thin Layer Chromatography (silica gel): 0.68 (benzene/acetone=2:1 by volume), 0.73 (chloroform/methanol=10:1 by volume);
Solubility: easily soluble in methanol and acetone, soluble in chloroform, and sparingly soluble in water and n-hexane; and

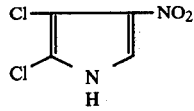

2. An antimycotic agent containing a carrier and an antimycotically effective amount of an active component SF-2080A substance represented by the following formula:

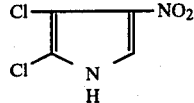

* * * * *